(12) United States Patent
Wolf, Jr. et al.

(10) Patent No.: US 8,202,269 B2
(45) Date of Patent: Jun. 19, 2012

(54) ELECTRICAL CAUTERY DEVICE

(75) Inventors: J. Stuart Wolf, Jr., Ann Arbor, MI (US);
Brian M. Yoder, Plymouth, MI (US);
Matthew J. Huddleston, Galena, OH
(US); Adam Landis, Reynoldsburg, OH
(US)

(73) Assignee: The Regents of The Universtiy of Michigan, Ann Arbor, MI (US)

( * ) Notice: Subject to any disclaimer, the term of this patent is extended or adjusted under 35 U.S.C. 154(b) by 1405 days.

(21) Appl. No.: 11/807,312

(22) Filed: May 25, 2007

(65) Prior Publication Data

US 2008/0294161 A1    Nov. 27, 2008

(51) Int. Cl.
*A61B 18/04*    (2006.01)
*A61B 18/18*    (2006.01)

(52) U.S. Cl. .............. 606/28; 606/27; 606/49

(58) Field of Classification Search ............ 606/41, 606/45, 49, 27–31
See application file for complete search history.

(56) References Cited

U.S. PATENT DOCUMENTS

| | | | |
|---|---|---|---|
| 3,886,944 A | | 6/1975 | Jamshidi |
| 4,074,719 A | | 2/1978 | Semm |
| 4,202,336 A | | 5/1980 | van Gerven |
| 4,314,559 A | * | 2/1982 | Allen .............. 606/45 |
| 4,449,528 A | | 5/1984 | Auth et al. |
| 5,019,076 A | | 5/1991 | Yamanashi et al. |
| 5,458,596 A | * | 10/1995 | Lax et al. ............ 606/31 |
| 5,573,533 A | * | 11/1996 | Strul .............. 606/34 |
| 5,593,406 A | * | 1/1997 | Eggers et al. .......... 606/29 |
| 5,851,206 A | * | 12/1998 | Guglielmi et al. ........ 606/28 |
| 5,954,680 A | * | 9/1999 | Augustine ............ 602/42 |
| 5,964,759 A | | 10/1999 | Yamanashi et al. |
| 5,984,950 A | | 11/1999 | Cragg et al. |
| 6,258,086 B1 | * | 7/2001 | Ashley et al. .......... 606/41 |
| 6,283,960 B1 | * | 9/2001 | Ashley ............. 606/32 |
| 6,416,534 B1 | * | 7/2002 | Montagnino et al. ...... 607/114 |

(Continued)

FOREIGN PATENT DOCUMENTS

WO    WO 2004/069300    *    8/2004

OTHER PUBLICATIONS

"Heaters Prototype Design Kit." Minco Products. N.p., n.d. Web. Jun. 22, 2011. <www.minco.com/.../Products/.../HDK01_Heater%20Kit%20Parts_Standard.pdf>.*

(Continued)

*Primary Examiner* — Linda Dvorak
*Assistant Examiner* — Jaymi Della
(74) *Attorney, Agent, or Firm* — Harness, Dickey & Pierce, P.L.C.

(57) ABSTRACT

An electrical surgical cautery device for delivering thermal energy to cauterize and provide hemostasis to a bleeding tissue comprises an electrically powered flexible thermal delivery element having a substantially planar resistive coil embedded in a thermally conductive material. The thermally conductive material comprises a tissue contact surface and a non-tissue contact surface. A power source is connected to the resistive coil of the thermal delivery element and provides an electrical current to heat the thermal delivery element being pressed against the tissue. A method for providing hemostasis to a bleeding tissue surface comprises providing and pressing an electrical cautery device having a thermal delivery element, against the hemorrhaging tissue at a predetermined temperature for an interval sufficient to cauterize the tissue and provide hemostasis.

18 Claims, 7 Drawing Sheets

U.S. PATENT DOCUMENTS

| | | | |
|---|---|---|---|
| 6,770,072 B1 | 8/2004 | Truckai et al. | |
| 6,773,409 B2 | 8/2004 | Truckai et al. | |
| 6,905,497 B2 | 6/2005 | Truckai et al. | |
| 6,913,579 B2 | 7/2005 | Truckai et al. | |
| 6,926,716 B2 | 8/2005 | Baker et al. | |
| 6,929,644 B2 | 8/2005 | Truckai et al. | |
| 7,011,657 B2 | 3/2006 | Truckai et al. | |
| 7,041,102 B2 | 5/2006 | Truckai et al. | |
| 7,070,597 B2 | 7/2006 | Truckai et al. | |
| 7,083,619 B2 | 8/2006 | Truckai et al. | |
| 7,087,054 B2 | 8/2006 | Truckai et al. | |
| 7,780,662 B2 * | 8/2010 | Bahney | 606/51 |
| 2002/0156451 A1 * | 10/2002 | Lenker | 604/500 |
| 2002/0177846 A1 | 11/2002 | Mulier et al. | |
| 2004/0199161 A1 | 10/2004 | Truckai et al. | |
| 2005/0021115 A1 * | 1/2005 | Yue | 607/114 |
| 2005/0096651 A1 | 5/2005 | Truckai et al. | |
| 2005/0159745 A1 | 7/2005 | Truckai et al. | |
| 2005/0171535 A1 | 8/2005 | Truckai et al. | |
| 2005/0192568 A1 | 9/2005 | Truckai et al. | |
| 2005/0203507 A1 | 9/2005 | Truckai et al. | |
| 2005/0261678 A1 | 11/2005 | Truckai et al. | |
| 2005/0267464 A1 | 12/2005 | Truckai et al. | |
| 2006/0111706 A1 | 5/2006 | Truckai et al. | |

OTHER PUBLICATIONS

American Society for Gastrointestinal Endoscopy; Endoscopic Hemostatic Devices; vol. 54, No. 6; May 2001; pp. 833-838.

Gregory T. Absten BSc.; MBA, Practical Electrosurgery For Clinicians; Sep. 2002; pp. 1-48.

JC Lantis II et al.; Comparison of Coagulation Modalities in Surgery; J. Laparoendosc Adv Surg. Tech. A.; Dec. 8, 1998; 1 Page (Abstract).

Fullarton et al.; Controlled Trial of Heater Probe Treatment In Bleeding Peptic Ulcers; Br J. Surg.; Jun. 1989; 1 Page (Abstract).

Deng et al.; Analytical Study on Bioheat Transfer Problems with Spatial or Transient Heating on Skin Surface or Inside Biological Bodies; Dec. 2002; vol. 124; pp. 638-649.

Olympus Corporation; Section 510(E), Submission to FDA; Mar. 19, 1985; 19 Pages.

\* cited by examiner

ELECTRICAL CAUTERY DEVICE

FIELD

The present disclosure relates to surgical devices and methods for providing hemostasis on actively bleeding wounds with large surface areas, and more particularly to a hand held electrical cautery device which is compressed against hemorraging tissue and which delivers precise thermal heating to permanently heat and coagulate bleeding tissue.

BACKGROUND

The statements in this section merely provide background information related to the present disclosure and may not constitute prior art.

During operative procedures, there is often the need for rapid hemostasis of wounds of parenchymal organs or from venous complexes with a large, actively-bleeding surface area. These wounds are created in over 1.5 Million procedures or traumatic events per year in the United States, including partial nephrectomies, partial hepatectomies, liver transplants, cholecystectomies, liver and spleenic trauma, and radical prostatectomies. The ability to staunch rapid bleeding from such wounds, due to either surgery or external trauma, is often found inadequate with thermal cauterization techniques and can result in high blood loss, termination of the surgery or even death. Consequently, there is a need for better methods of achieving hemostasis in order to allow needed and safer operations. This need is particularly acute in minimally-invasive surgery, a surgical technique that utilizes small laparoscopic ports to access the operative area, rather than large-skin incisions.

Broadly, there are four current methods for obtaining surgical hemostasis: tissue compression using surgical sponges or sutures, use of sutures or clips, application of biological agents and adhesives, and heat cauterization.

Tissue compression hemostasis describes a process whereby pressure is applied to the bleeding surface using a variety of substances, most commonly in the surgical operating theater using cotton gauze. The pressure causes the blood vessels supply the area to collapse and, thereby, stop bleeding temporarily. This technique is most commonly used to obtain temporarily hemostasis prior to attempting permanent hemostasis with another method. Permanent hemostasis can be obtained with compression, however, only if sufficient time is allowed for the patient's natural hemostatic mechanisms to form an adequate clot, and if the patient's natural hemostatic mechanisms are functional. This process is too time-consuming for practical use in the operating room, and clot hemostasis may be less durable than that provided by cautery. Furthermore, release of the clot into the circulation can cause problems in remote areas, such as the brain, heart and lungs.

Biochemical agents can speed the patient's own coagulation cascade and, when applied to the wound, result in more rapid hemostasis. On large, actively-bleeding wounds, these agents are rapidly washed away; attempts at preventing this overlying material have met with mixed success. Tissue adhesives come out, which may be a recapitulation of the clotting cascade or may be completely synthetic and can form an adherent, impervious layer over the wound, but only if they are not dispensed by bleeding and can form a bond with the tissue. Therefore, while promising, biological agents and adhesives have not yet reached the efficacy required for large, actively-bleeding wounds of parenchymal organs or from venous complexes.

Heat cauterization is the oldest and most commonly used hemostatic technique for these wounds. Heat is applied to the wound surface, causing protein coagulation, which plugs the bleeding points and stops the bleeding. Currently, heat cautering operative procedures are almost exclusively achieved via diathermy. For diathermy, the patient is electrically grounded to an AC power source. The grounding is achieved over a very large surface area, distant from the area of operation. A surgical device that completes the circuit is applied to the wound. The complete electrical circuit results in current flow through the tissue between the device and the ground. The current results in electrical resistance heating according to the electrical formula $R=V/I$, with I being the current density, which is inversely proportional to the cross-sectional area available to the current. The resistance heating coagulates proteins on the wound surface, causing hemostasis. The inverse relationship of current density and cross-sectional area limits the area that can be effectively addressed.

The most common variations of diathermy are electrical cautery, bi-polar cautery and argon beam coagulation. Amongst all methods, argon beam coagulation would be the most direct competitor to this technology. Argon beam coagulation employs a charged device that sprays a stream of argon gas onto the wound. The circuit is completed as the gas provides a guide for an electrical arch to form between the device and the wound area in contact with the gas cloud. There is no compression with this device, but the stream of argon gas is effective as "blowing" blood off the surface of the wound, thereby obviating the dispersion of energy by blood that renders standard electrical cautery ineffective in the operative setting when used to address a more rapidly bleeding wound. There also is no risk of disrupting the coagulum when the device is withdrawn. There is, however, current flow through the patient between the instrument tip and the ground, with the previously-mentioned side effects, as well as a risk of gas embolism. Additionally, the argon gas flow is insufficient to remove the blood from more briskly bleeding wounds. Finally, the area that can be addressed at a given instant with argon beam coagulation is relatively small.

All of the hemostasis methods listed above have advantages and disadvantages, but none sufficiently addresses the challenges associated with large, briskly-bleeding, parenchymal or venous-complex wounds, particularly when they occur during minimally invasive (laparoscopic) operative procedures. Notwithstanding the great effort to make all surgery as minimally-invasive as possible, difficulties with these wounds hamper not only current surgical care, but also the development of new minimally-invasive procedures. The present technology addresses the needs described above to temporarily staunch blood flow and coagulate blood vessels by providing thermal energy in the form of electrical resistance at a temperature optimized for tissue cautery to permanently coagulate bleeding tissue. Such a device can more effectively stop hemorrhaging from parenchymal organs or venous complexes than the prior art, and can be adapted to a minimally-invasive surgery environment.

SUMMARY

The disclosure provides an apparatus for delivering thermal energy to tissue. The apparatus comprises an electrically powered flexible thermal delivery element having a substantially planar resistive coil embedded in a thermally conductive material. The thermally conductive material comprises a tissue contact surface and a non-tissue contact surface. The tissue contact surface is operable to heat the surface of the tissue being compressed. The thermal delivery element has a maximum wattage density of 5-100 watts/in$^2$, sufficient to heat a flexible thermal delivery element in contact with the bleeding tissue to a set predetermined temperature. A controller/power generating means is electrically connected to the resistive coil of the thermal delivery element and applies an electrical current to the thermal delivery element during a thermal application interval having sufficient energy to heat the tissue contact surface of the thermal delivery element to the preset predetermined temperature to cauterize the tissue during the thermal application interval.

The present disclosure also provides for a surgical cauterizing device. The device comprises a power generating means for example a controller/power supply providing a source of current or voltage, an applicator tool instrument having a first end and a second end wherein first end is in electrical communication with the power source, an electrical lead disposed within the applicator tool instrument, a thermocouple and a deformable bio-inert thermal delivery element operably connected with the second end of the applicator tool instrument. The thermal delivery element has an electrically resistive planar foil disposed within a thermally conductive material to generate heat.

In another aspect, the present disclosure provides for a method of heating tissue comprising the steps (a) providing a surgical cauterizing device including a power source, a control shaft and a flexible thermal delivery element having a planar resistive coil; (b) applying electric power to the thermal delivery element for a period of time sufficient to heat the thermal delivery element to a predetermined temperature; and (c) compressing the thermal delivery element of the device at the predetermined temperature against the tissue for a thermal application interval sufficient to cauterize the tissue during thermal application interval.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
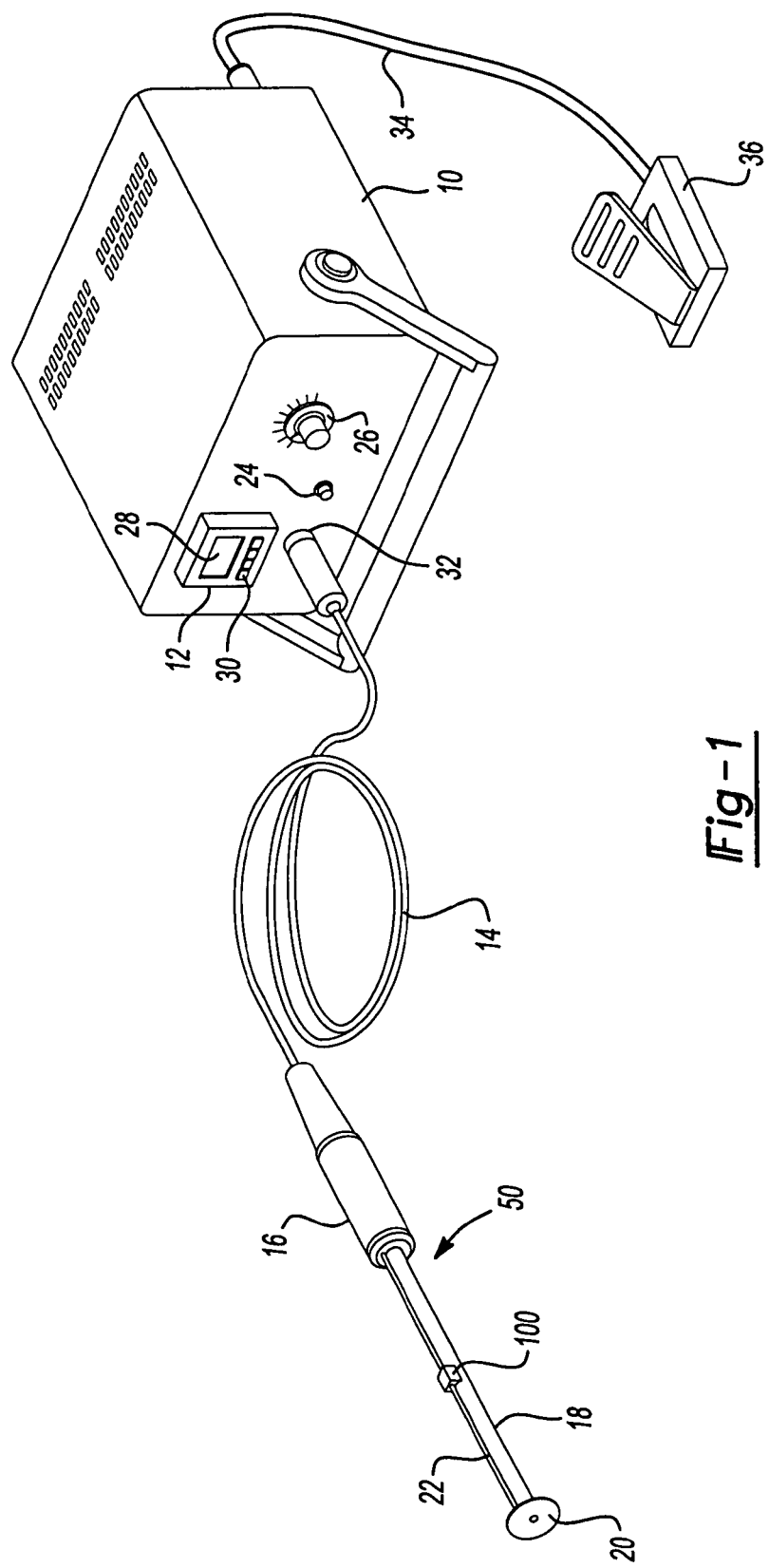
FIG. 1 illustrates a perspective view an embodiment of the electro-thermal cautery device connected to a controller/power supply and foot switch in accordance with the present disclosure.

The following description is merely exemplary in nature and is not intended to limit the present disclosure, application, or uses. It should be understood that throughout the drawings, corresponding reference numerals indicate like or corresponding parts and features.

The present disclosure provides for an electrical cautery device configured for surgical use. The device can be operated by an individual surgeon or operator to cauterize large surface areas of actively bleeding tissue to effect hemostasis and thereby stop bleeding in human or animal patient.

The electrical cautery device is illustrated in FIG. 1. The device includes a power generating means such as a controller/power supply 10 having a temperature input means 12 containing visual temperature indicator 28 and temperature selection buttons 30. The controller/power supply 10 further provides a variable voltage selection dial 26 and a power on warning light 24. A grounded cable 14 can be insulated and is plugged into the cautery tool connector 32 at a first end and to the applicator tool handle 16 at a second end. The applicator tool tube 18 is typically inserted into the applicator tool handle 16.

In some embodiments, the applicator tool tube 18 can be fixedly attached to a wiring bundle 22, the bundle can comprise one or more wires originating from the controller/power supply 10. In some embodiments, the wires of the wiring bundle 22 can include a conductor wire carrying power from the controller/power supply 10 to the thermal delivery element 20. In some embodiments, the wiring bundle can also carry a wire from the controller/power supply 10 to at least one thermocouple or resistance temperature detector (RTD) 54 operably connected to the thermal delivery element 20. In some embodiments, the wiring bundle 22 can also be concealed within the applicator tool tube 18 and inserted into the applicator tool handle 16 and grounded cable 14 therethrough. The applicator tool tube 18 and applicator tool handle 16 can be grounded for operator safety.

In practice the surgeon or operator would use the applicator tool and thermal delivery element in a similar fashion to a laparoscopic device. To heat and/or cauterize the desired tissue, the surgeon actuates the foot switch 36 connected to the controller/power supply 10 to apply power to the thermal delivery element 20 while compressing the thermal delivery element 20 onto the patient's tissue to be cauterized.

Figure 2:
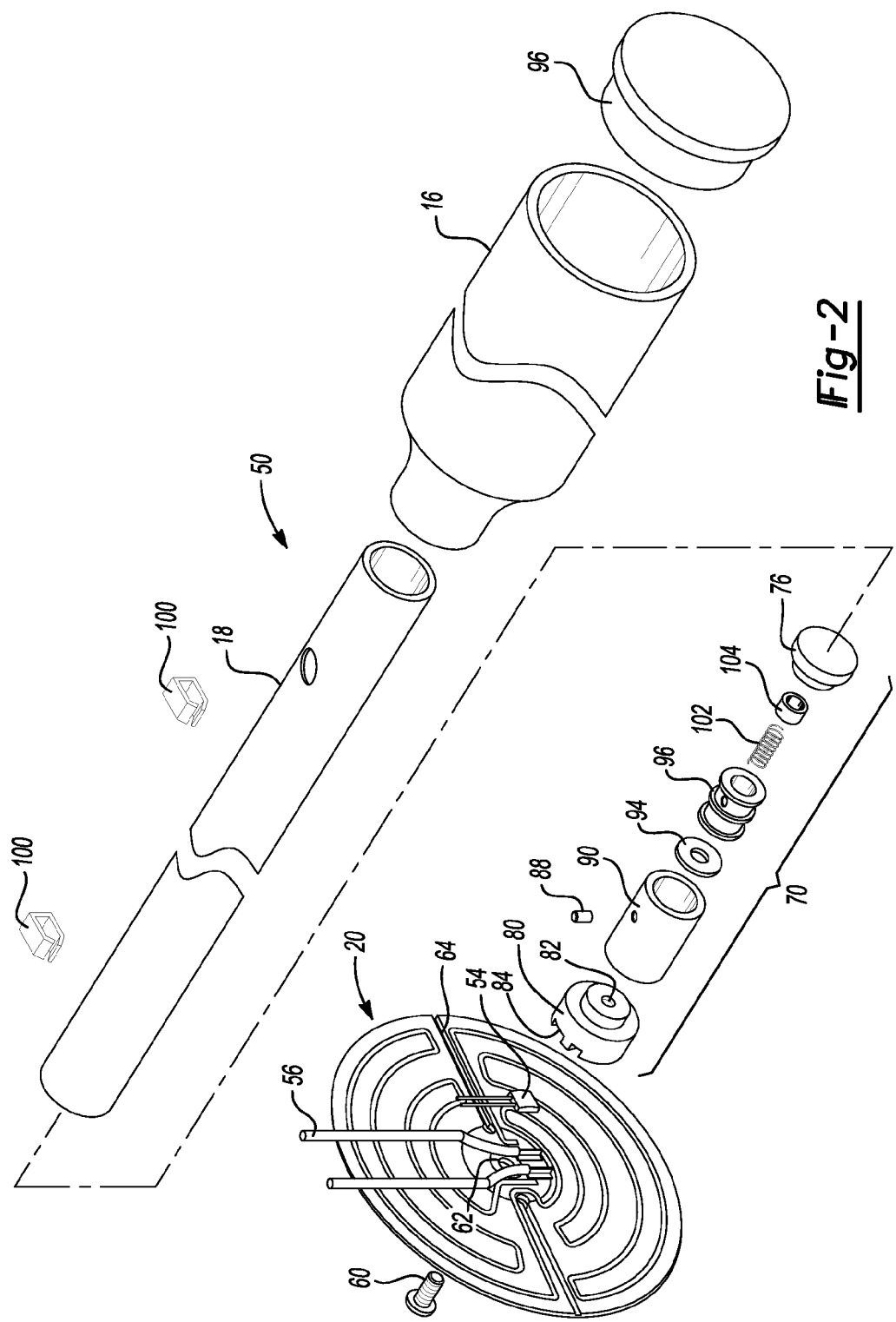
FIG. 2 illustrates in an exploded view an embodiment of the applicator tube operably connected to the thermal delivery element in accordance with the present disclosure.

The applicator tool 50 when connected to the thermal delivery element 20 is best illustrated in FIG. 2. The applicator tool 50 comprises an applicator tool handle 16 that can be capped with a handle cap 96. The applicator tool handle 16 can also be connected to a first end of an applicator tool tube 18 in an axial orientation. The walls of the applicator tool tube 18 can be relatively thin, ranging from about 0.5 mm to about 5.0 mm. The diameter of the applicator tool tube 18 can vary from 0.3 cm to about 3.0 cm, from about 0.5 cm to about 2.0 cm, or from about 1.0 cm to about 1.5 cm.

The applicator tool tube 18 can further contain wire guides 100 to fasten wires (not shown) emanating from the applicator tool tube 18 and run externally along the tube to the thermal delivery element 20. The applicator tool 50 including the applicator tool tube 18 and applicator tool handle 16 can be made of any sterilizable material, including metal, ceramic or hardened plastics. In some embodiments, the metal can be surgical steel, metal alloys and mixtures thereof. In some embodiments, the applicator tool handle 16 and the applicator tool tube 18 can comprise stainless steel. In some embodiments, the length of the applicator tool 50 can range from 10 cm to about 100 cm.

The shape of the applicator tool tube 18 and applicator tool handle 16 can be varied. The applicator tool tube 18 and applicator tool handle 16 can be shaped cylindrically as shown in FIGS. 1 & 2, or alternatively, they can be square, triangular, or any customizable shape that is medically useful.

Contained within the applicator tool tube 18 is a quick connect assembly illustratively shown as 70 in an exploded format for attaching the thermal delivery element 20 to the applicator tool 50. Spaced circumferentially, is a heater adapter 80, a center bore 82 positioned therethrough, and a bore guide 84 that mates with the thermal delivery element 20. In some embodiments, the thermal delivery element 20 is further guided for quick attachment to the applicator tool 50 by positioning an end cap 76 to the end of the applicator tool 50.

As further shown in FIG. 2, a thermal delivery element 20 is shown in an exploded view for assembly of the thermal delivery element 20 and connection to the applicator tool 50. The thermal delivery element 20 is shown in greater detail in FIGS. 3 and 4. In various embodiments, the thermal delivery element 20 can be any flexible, deformable, planar structure that can upon pressure, deform to the shape of the tissue surface being compressed by the thermal delivery element 20. In various embodiments, the shape of the thermal delivery element 20 can be generally planar or can vary. The thermal delivery element 20 can be circular, square, rhomboid, triangular or any shape that can be manufactured.

As shown in FIG. 2, the quick connect assembly 70 can be generally placed inside the applicator tool tube 18 lumen. In some embodiments, the thermal delivery element 20 can be affixed to the applicator tool 50 by means of a fastener 60. The fastener 60 can be any commonly used fastening material, including, without limitation, a screw, a rivet, an insert and the like. The fastener 60 is inserted through the thermal delivery element 20 and a heater adapter 80 center bore 82. The thermal delivery element 20 can be connected to the applicator tool 50 by a quarter turn of the quick connect assembly 70. The quick connect assembly 70 comprises a heater adapter 80. The heater adapter 80 can connect to the thermal delivery element 20 by aligning the bores 62 and 82 and turning the thermal delivery element a quarter turn when the heating adapter 80 is engaged with thermal delivery element 20. In some embodiments, the applicator tool 50 can be attached to the thermal delivery element 20 by pressing the applicator tool 50 into the thermal delivery element 20 the connection is keyed and once pressed, spring 102 presses the heater tab 104 into position and locks the pin 88 into the guide 90 and through guide 96 and washer 94 into a locked position.

In some embodiments, the thermal delivery element 20 can also be operably coupled to the at least one thermocouple or resistance temperature detector (RTD) 54 as shown in FIG. 2. In some embodiments, the thermocouple or resistance temperature detector (RTD) 54 attached to the thermal delivery element 20 can be any temperature measuring device including, for example, thermometers, resistance temperature detector (RTD) or RTD sensors, thermistor sensors, semiconductor sensors or thermocouple sensors. In some embodiments, the thermocouple or resistance temperature detector (RTD) 54 (not shown) sends an electrical signal to the controller/power supply 10 (not shown) along wiring bundle 22 and can terminate in wires leading to the thermocouple or resistance temperature detector (RTD) 54. In some embodiments, the thermocouple or resistance temperature detector (RTD) 54 can include, for example, platinum RTDs commercially available from Heraeus Electro-Nite Co. (Philadelphia, Pa. USA). In some embodiments, wiring bundle 22 originating from the controller/power supply 10 (not shown) can extend to the thermal delivery element 20. The wiring bundle 22 can include a single wire carrying a wire connecting the thermocouple or resistance temperature detector (RTD) 54 to the controller/power supply 10 (not shown). In various embodiments, the wiring bundle 22 can include two or more wires, including conductor wire 56 terminating on the thermal delivery element 20. Conductor wire 56 can be in electrical communication with the controller/power supply 10 and provide power from the controller/power supply 10 to the thermal delivery element 20. Wiring bundle 22 can be carried within the grounded cable 14 of FIG. 1 and extend down the applicator tool 50 within the applicator tool tube 18 or along the exterior of the applicator tool tube 18 (as illustrated in FIG.1 as wiring bundle 22). When wiring bundle 22 is extended along the applicator tool tube 18, the wiring bundle 22 can be clipped to the applicator tool tube 18 with wire guides 100.

Figure 3:
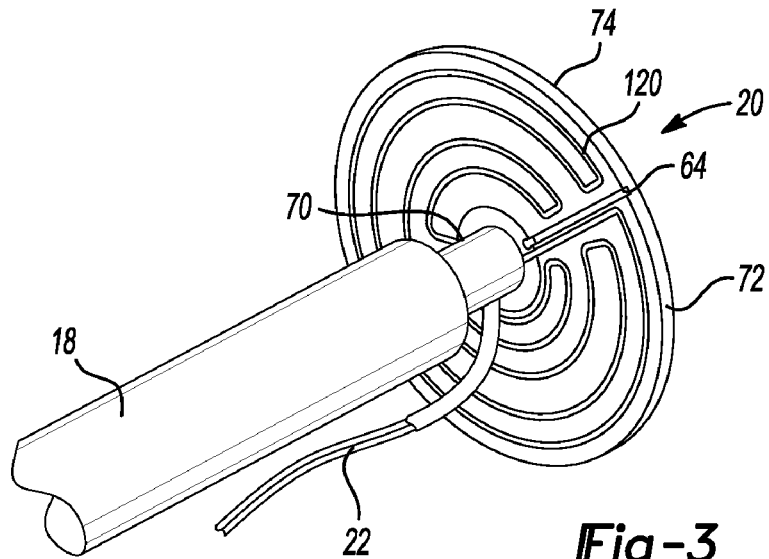
FIG. 3 illustrates a plan elevational view of the thermal delivery element 20 connected to an applicator tool tube 18.
Figure 3A:
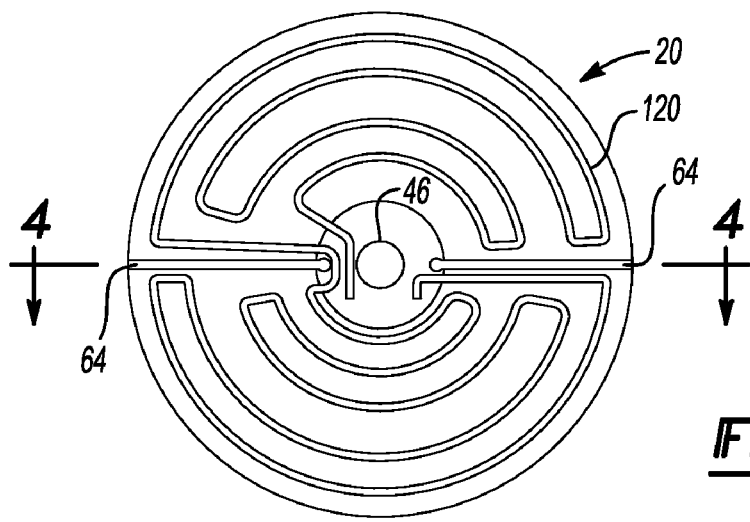
FIG. 3A shows a plan view of the thermal delivery element in accordance with the present disclosure.

FIG. 3 and FIG. 3A further illustrates a typical thermal delivery element 20 in a partial schematic view. FIG. 3 shows a plan elevational view of the thermal delivery element 20 connected to an applicator tool tube 18. FIG. 3A shows a plan view of the thermal delivery element 20. As illustrated in FIG. 3, the thermal delivery element 20 can be attached to the applicator tool tube 18 as shown prior to use. The thermal delivery element 20 can comprise a resistive coil 120. In some embodiments, the resistive coil 120 can be any resistive material that will generate heat when a source of electrical power, current and/or voltage is applied to the resistive coil 120. In some embodiments, the resistive coil 120 can be a metal or a metal containing material having a variable current resistance from about 10 $\Omega/in^2$ to about 500 $\Omega/in^2$. In some embodiments, the resistive coil 120 can be a copper resistive coil 120 having a maximum wattage density of about 1 watt/$in^2$ to about 100 watts/$in^2$, or from about 5 watts/$in^2$ to about 70 watts/$in^2$. As shown in FIG. 3, the resistive coil 120 can be connected to wiring bundle 22. In some embodiments, wiring bundle 22 can transport current or voltage from the thermocouple or RTD on the thermal delivery element 20 along the applicator tool tube 18 and connect electrically to the controller/power supply (not shown).

The power, current or voltage originating from the controller/power supply 10 can be transported along a wiring bundle 22 and ultimately through the applicator tool tube 18 and connect electrically to the thermal delivery element 20 through the aperture of quick connector assembly 70 The pattern and number of loops distributed in the resistive coil 120 is generally variable, provided that adequate heat dissipation is distributed evenly throughout the surface area of the thermal delivery element 20. In some embodiments, the resistive coil 120 can be any thermally resistive coil and can be obtained commercially, for example from Minco Products Inc., Model No. HK913F or HK 913J (Minneapolis, Minn. USA).

The resistive coil 120 is embedded in one or more thermally conductive materials capable of transferring the heat generated by the resistive coil 120. The thermal delivery element 20 is generally planar and can be designed and manufactured in any shape. In some embodiments the thermal delivery element 20 can be circular as shown in FIGS. 3 and 3A, however, one skilled in the art can manufacture any shape having a resistive coil 120 embedded in a thermal delivery element 20 having one or more layers of thermally conductive materials 150 and 152.

As illustrated in FIG. 3A a plan elevational view of outer or tissue contact surface 74 is shown. In some embodiments, the thermal delivery element 20 is generally flexible allowing distortion in the inner surface 72 and tissue contact surface 74 to enable compression of hemorrhaging tissue. To cater for the degree of flexibility required, slits 64 are placed on the thermal delivery element in diametrically opposite positions in the thermal delivery element 20, The number and length of slits 64 are typically not prescribed and can be modified according to the size and shape of the thermal delivery element 20, or the degree of deformability required for the thermal delivery element 20. By way of a non-limiting example, a thermal delivery element 20 is shown in FIG. 3A as being circular in shape and has a pair of slits 64. The thermal delivery element 20 can be attached to the applicator tool tube 18 (not shown) using a fastening means 46. In some embodiments, the fastening means 46 can be for example, a screw, a rivet, a cylinder or any commonly known fastening materials to fasten a planar material to a cylindrical tube. The fastening means 46 can be made of any durable material that can withstand heat from about −50° C. to about 300° C. without significant deformation or melting. In some embodiments, the fastening means 46 is a metallic rivet, or a metallic screw.

Figure 4:
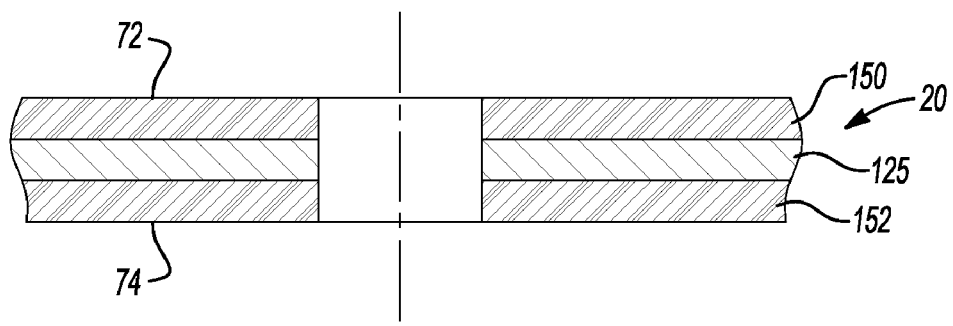
FIG. 4 illustrates a cross-sectional view of an embodiment of the thermal delivery element in accordance with the present disclosure.

With reference to FIG. 4, the thermal delivery element 20 is cut in cross-section to illustrate the various layers or components in accordance with the present disclosure. In some embodiments, the resistive coil 120 can be embedded in a thermally conductive adhesive material 125. The thermally conductive adhesive material can be any thermally conductive material such as Teflon®, polytetrafluoroethylene, Fluoro-ethylene propylene, polyimide, or acrylic based material.

The thermal delivery element 20 has two surfaces, a first or inner surface 72 and a tissue contact surface 74. In some embodiments, the inner and tissue contact surfaces 72, and 74 are identical. In some embodiments, the composition of the material of the tissue contact surface 74 can be different to the composition of the inner surface 72. In some embodiments, the wiring bundle 22 depicted in FIG. 3, incorporating for example, a conductor wire and/or a thermocouple or resistance temperature detector (RTD) wire can be connected to the resistive coil 120 and the inner surface 72 respectively as a means to conduct current and/or power to the resistive coil 120 and/or to measure the temperature of the thermal delivery element 20.

Continuing to refer to FIG. 4, the thermal delivery element 20 is shown cut in transverse section. The resistive coil 120 shown in FIG. 3 (shown in plan elevation), can be generally embedded in adhesive 125. The thermally conductive materials 150 and 152 can comprise at least one deformable material that can conduct heat at temperatures ranging from about 0° C. to about 250° C. In some embodiments layers of thermally conductive materials 150 and 152 may be different or they may be the same. Thermally conductive material 150 has a inner surface 72, of the thermal delivery element 20 and thermally conductive material 152 has a tissue contact surface 74 of the thermal delivery element 20. The thickness of thermally conductive materials 150 and 152 can vary from about 0.01 mm to about 5 mm. In some embodiments, one or multiple layers of different thermally conductive material(s) can be manufactured to form each of the thermally conductive materials 150 and 152. A skilled practitioner can vary the chemical and physical characteristics of the thermally conductive materials 150 and 152 to suit the cautery conditions and thermal transfer characteristics desired. In some embodiments, the glass transition temperature (Tg) of the thermally conductive materials 150 and 152 can be in the range of about 250° C. to about 500° C., and can have tensile strengths of about 150-350 MPa at 21° C. and about 75-250 MPa at 200° C. using the ASTMD-882-91, Method A test.

Illustratively, a resistive coil 120 can be adjacent to two thermally conductive materials 150 and 152, each material forming at least one surface. In some embodiments, the thermally conductive material 150 can comprise a single thermally conductive layer comprising the material, Teflon®, and can have at least one surface, namely, the inner surface 72. Thermally conductive material 152 can comprise a single layer comprising, for example the thermally conductive material, polyimide or Kapton®, and can have at least one surface, namely the tissue contact surface 74. In some embodiments, the polyimide material comprises Kapton®. As mentioned above, the number of thermally conductive materials arranged in layers can vary and can include one or more distinct compositional layers. In some embodiments, each layer can comprise one or more thermally conductive materials and the layer can also incorporate non-thermally conductive materials, provided that the net composition of the layer is thermally conductive. It is generally preferred that the tissue contact surface 74 and/or thermally conductive material 152 be composed of a substantially non-stick material which when the tissue contact surface 74 is elevated to above 50° C. and is pressed against animal tissue, including human, the thermal delivery element 20, and more particularly, the tissue contact surface 74 will not substantially stick to the tissue or blood at the site of cauterization.

Figure 5A:
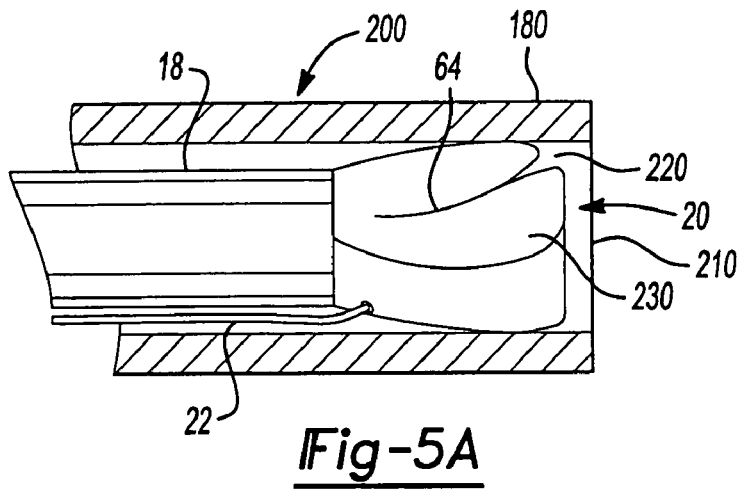
FIG. 5A illustrates an embodiment of an applicator tool tube within the lumen of a laparoscopic device prior to unfolding of the thermal delivery element in accordance with the present disclosure.
Figure 5B:
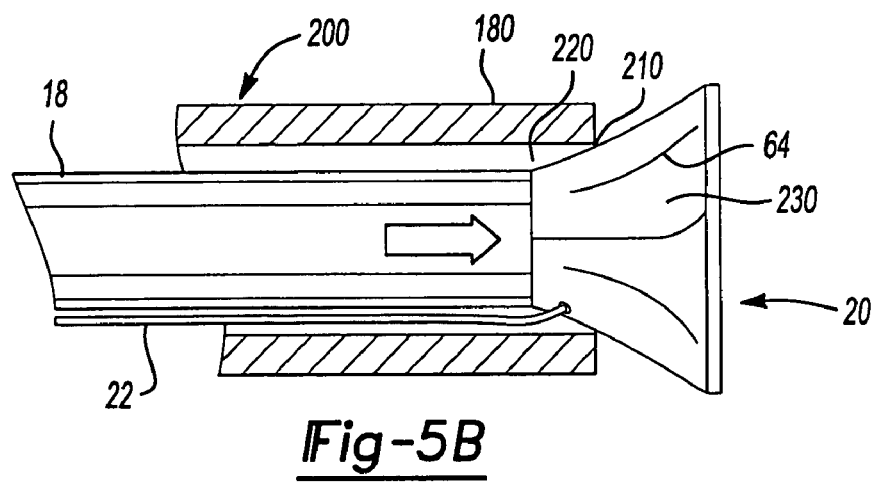
FIG. 5B illustrates the same applicator tube being pushed forward and partially exiting the laparoscopic device in accordance with the present embodiment.
Figure 5C:
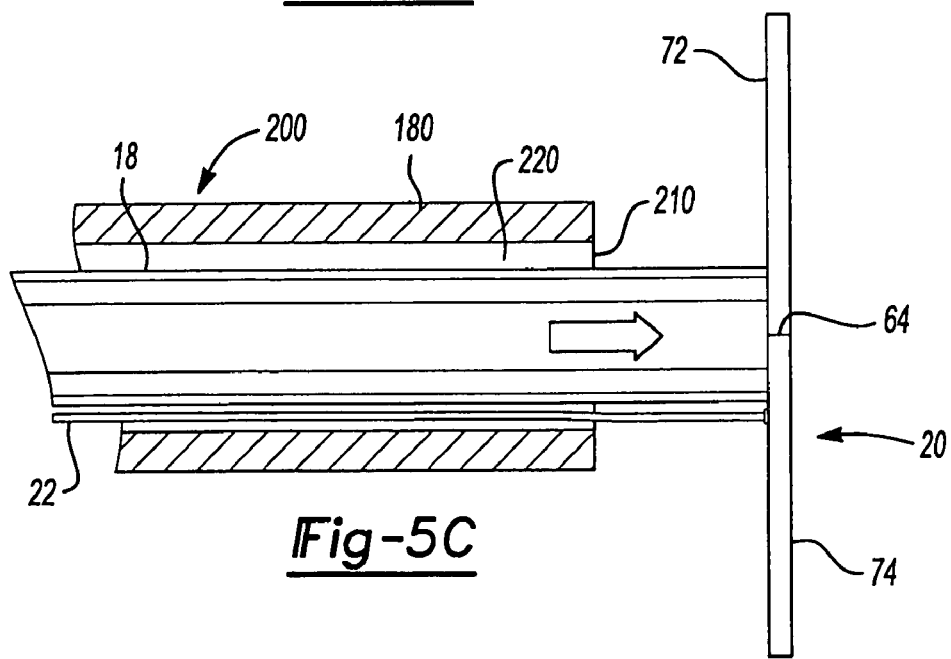
FIG. 5C illustrates the applicator tool tube partially exiting the laparoscopic device along with the complete unfolding of the thermal delivery element in accordance with the present disclosure.

FIG. 5A-5C illustrates a second embodiment and an actual application of a surgical electrical cautery device of the present technology. The laparoscopic surgical instruments generally include a laparoscope for viewing the surgical field and working tools defining the surgical implements. The laparoscopic device 200 can be a surgical laparoscopic device and can have the thermal delivery element 20 retracted into the lumen 220 of the laparoscopic tube 180.

In some embodiments, the thermal delivery element 20 as shown in FIG. 5A can have a plurality of slits 64 which can vary depending on the diameter of the thermal heating element 20 and on the internal diameter of the lumen 220. The slits 64 define the periphery of the thermal delivery element leaves 230 that are folded upon each other when the thermal delivery element 20 is retracted into the lumen 220 of the laparoscopic tube 180. In some embodiments, a thermal delivery element 20 having a diameter ranging from about 1 inches (2.54 cm) to about 2 inches (5.08 cm) can have two or more slits 64. In some embodiments, the thermal delivery element 20 has two to four slits 64, enabling the element to retract into the laparoscopic tube. In addition to the thermal delivery element 20 having slits 64 that allows the thermal delivery element leaves 230 to be folded onto itself as shown in FIG. 5A, the applicator tool tube 18 and the thermal delivery element 20 can be slidably moved within the laparoscopic tube 180.

The applicator tool tube 18 and the thermal heating element 20 can slide out of the lumen 220 as indicated by the arrow and through the exit port 210 as shown in FIG. 5B. As the applicator tool tube 18 and thermal delivery element 20 exit through the laparoscopic exit port 210, the thermal delivery element leaves 230 can unfold to a natural position as shown in FIG. 5C. As illustrated in FIG. 5C, the applicator tool tube 18 operatively connected to the thermal delivery element 20 is shown fully extended and is ready for operation. In some embodiments, the wiring bundle 22 can provide current or power to the thermal heating element. The wiring bundle 22 can be disposed outside the applicator tool tube 18 or, alternatively, can be placed within the applicator tool tube 18 and connect with the thermocouple or resistance temperature detector RTD (not shown) operably connected with the thermal delivery element 20. In some embodiments of the present disclosure, the laparoscopic tube 180 can also optionally house one or more surgical implements and functions, for example, a scalpel, a camera, an irrigation tube, a vacuum line, a light, a pair of surgical forceps and any other surgical implement that can fit within the lumen 220 along with the surgical cautery device described herein.

In some embodiments, the laparoscopic tube 180 can be manufactured from any appropriate surgical material commonly used in the art of surgical instrumentation. Since the laparoscopic tube 180 is generally inserted into the patient, it must be able to withstand any one of heat, chemical or radiation sterilization without distortion or structural failure. In some embodiments, the laparoscopic tube 180 can be made from metal, ceramic or thermoresistive plastics. In some embodiments, the laparoscopic tube is made of surgical steel and can be made to any length commonly used in other surgical laparoscopic devices and which can house the electrical cautery device.

Figure 6A:
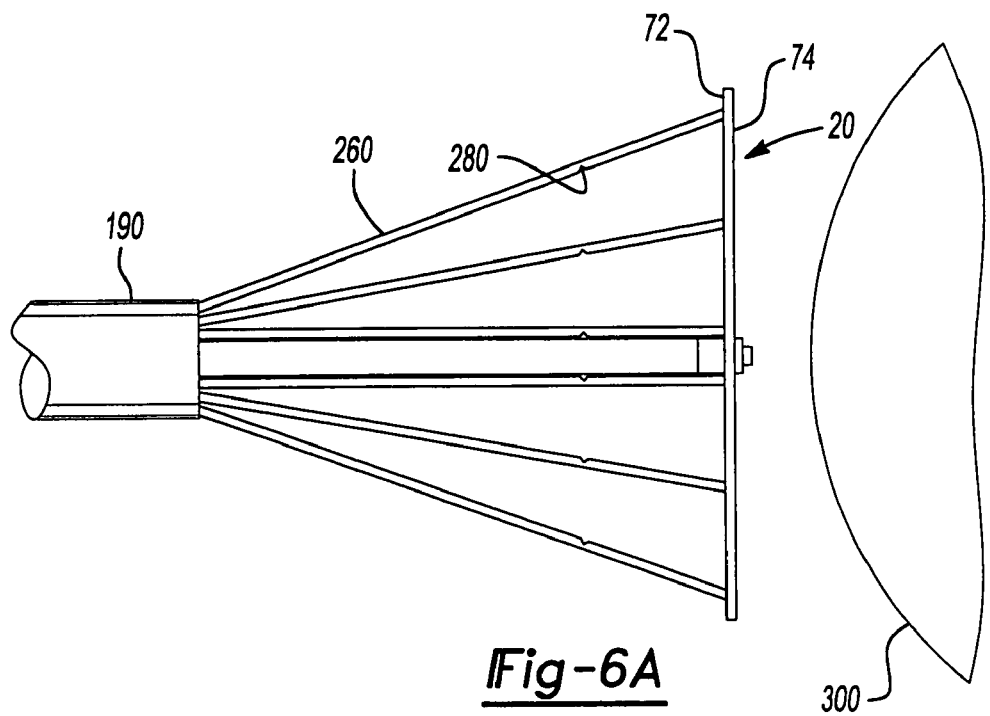
FIG. 6A illustrates an embodiment of the thermal delivery element supported by radially projecting arms prior to deformation in accordance with the present disclosure.
Figure 6B:
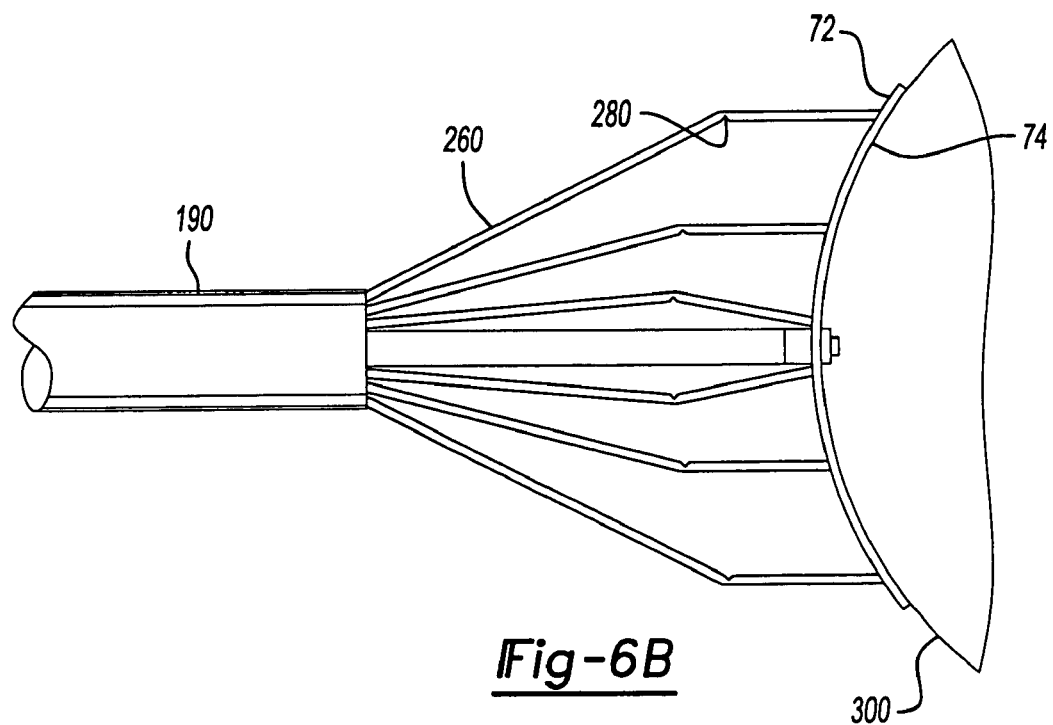
FIG. 6B illustrates an embodiment of a thermal delivery element being pressed against the irregular tissue by the radially projected arms in a deformed state in accordance with the present disclosure.

FIGS. 6A & 6B illustrates a surgical cautery device which is similar to the cautery device shown in FIG. 3 above except that the thermal delivery element 20 is being supported by a plurality of arms 260 having an indentation, for example a notch 280. The plurality of arms 260 can be attached to a modified applicator tool tube 190 at a first end and to the thermal delivery element 20 at the second end. In some embodiments, the arms radially project from the modified applicator tool tube 190 and connect around the periphery of the thermal delivery element 20. Each arm can have at least one notch 280 that can permit the deformation of the thermal delivery element 20 when pressing tissue 300 that does not have a planar surface contour. When the thermal delivery element 20 is not being pressed against tissue 300, the thermal delivery element 20 remains planar and the arms 260 remain linear, as shown in FIG. 6A. As illustrated in FIG. 6B, when tissue 300 is in need of hemostasis or otherwise requires cauterization, for example, during surgery to remove tissue or after trauma, the tissue contact surface 74 of the thermal delivery element 20 can be pressed against tissue 300, and the resistance inherently possessed by the arms 260 is offset by deformation of the arms 260 at the notch 280.

Methods of Use

Figure 7:
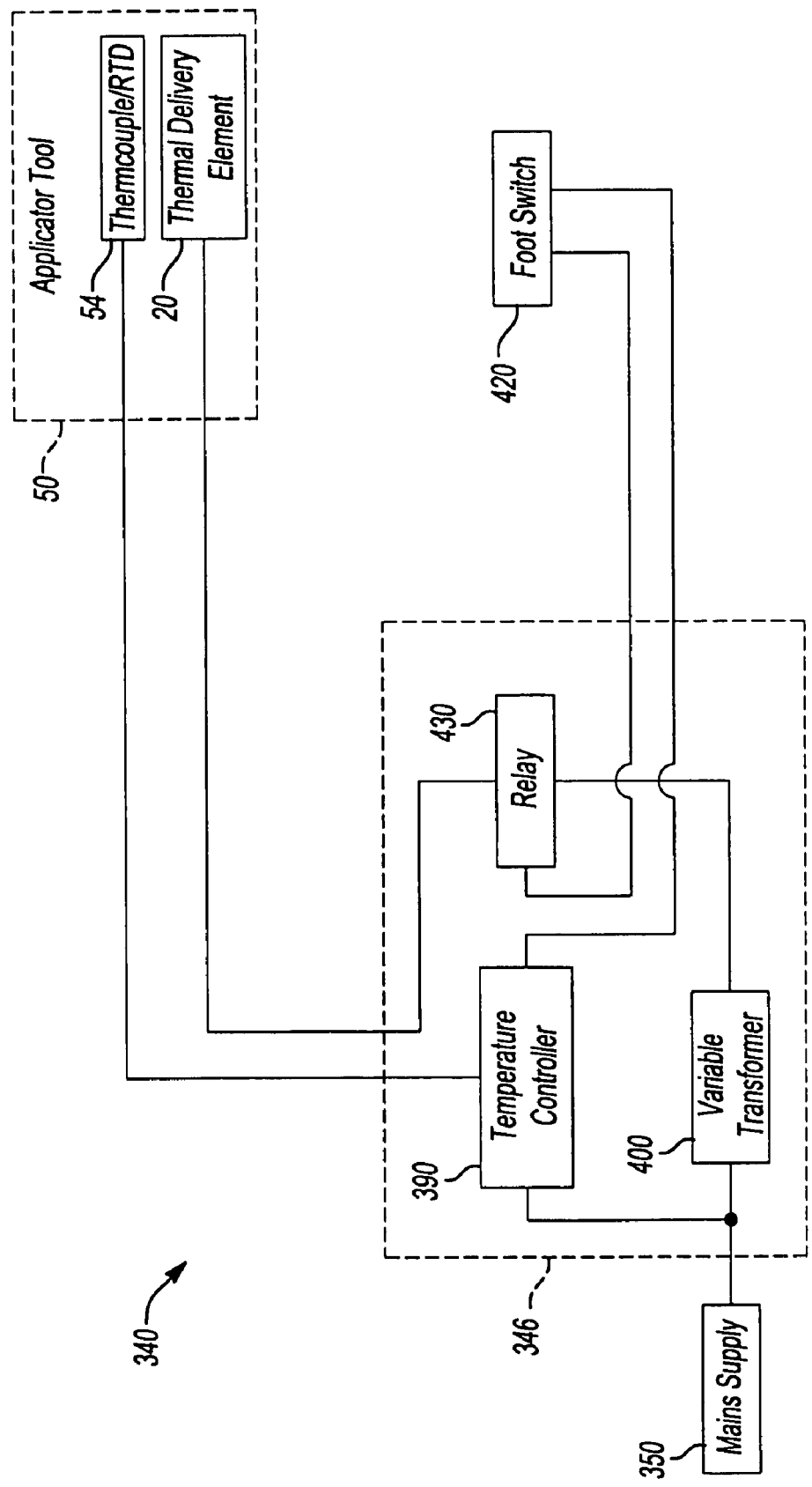
FIG. 7 illustrates a functional block diagram of an electrical cautery device 340 in accordance with the present disclosure.

Referring now to FIG. 7, a functional block diagram of an electrical cautery device 340 according to the principles of the present disclosure is presented. The electrical cautery device 340 includes an applicator tool 50 and a controller/power supply 346. The applicator tool 50 includes a thermal delivery element 20 and a thermocouple or resistance temperature detector (RTD) 54. The applicator tool 50 may be connected to the controller/power supply 346 via a grounded cable.

The controller/power supply 346 includes a temperature controller 390, a variable transformer 400, and a relay 430. The temperature controller 390, the variable transformer 400, and the relay 430 may be implemented in a single device, or may be distributed among two or more devices. The variable transformer 400 and the temperature controller 390 receive power from a mains supply 350. The mains supply 350 may include current protection and user protection elements, such as ground fault circuit interrupters, fuses, and/or circuit breakers.

The variable transformer 400 can be set to deliver a predetermined amount of power to the thermal delivery element 20. The power may be provided to the thermal delivery element 20 via the relay 430. The temperature controller 390 can be set to a predetermined temperature. The temperature controller 390 receives temperature data from the thermocouple or resistance temperature detector (RTD) 54. Until the thermocouple or resistance temperature detector (RTD) 54 indicates that the predetermined temperature has been reached, the temperature controller 390 may send a control signal to the relay 430. The control signal causes the relay 430 to pass the power from the variable transformer 400 to the thermal delivery element 20.

Once the predetermined temperature has been reached, the temperature controller 390 may remove the control signal from the relay 430, causing the relay 430 to stop the flow of power to the thermal delivery element 20. The control signal may be transmitted to the relay 430 via a foot switch 420. When the foot switch 420 is not engaged, the control signal is not received by the relay 430, and power is not transmitted to the thermal delivery element 20.

The predetermined temperature programmed into the temperature controller 390 may be selected from one or more ranges. For instance, temperature ranges may include from 80° C. to 250° C., from 90° C. to 200° C., from 100° C. to 150° C., and from 110° C. to 120° C. The variable transformer 400 may control output power by adjusting output voltage within a range, such as from 0-120 VAC or from 0-240 VAC. For example, the variable transformer 400 may be set to approximately 75% power (which may correspond to 90 VAC) in order for the thermal delivery element 20 to reach a temperature of about 120° C. within 30-240 seconds.

The temperature controller 390 receives the actual temperature of the thermal delivery element 20 via input from the thermocouple or resistance temperature detector (RTD) 54. Upon reaching the desired set point temperature, the temperature controller 390 can cut off power delivered to the applicator tool 50. In use, the surgeon can actuate the variable transformer 400 by depressing the foot switch 420 for a predetermined period or until the set point temperature has been reached and then for an additional period to cauterize the tissue in contact with the thermal delivery element 20 to a desired depth ranging from 0 to about 5 mm or more. In some embodiments, actuation of the variable transformer 400 can be performed by pressing a switch (not shown) on the applicator tool 50, for example on the applicator tool handle 16, rather than the foot switch 420.

Supply of current to the variable transformer 400, is provided by the mains supply 350. The surgeon is protected from current overload by installation of an optional fuse 360 and ground fault protector 370. Release of the foot switch 420 also interrupts power delivery to the applicator tool 50. The variable transformer 400 can control the output voltage and can be adjustable from a range of 0-120 VAC. During use, the variable transformer 400 can be set to 90 VAC (approximately 75% power) for reaching thermal delivery element temperature of about 120° C. within 30-240 seconds.

Typical usage of the electrical cautery device will now be described with reference to FIG. 1. The electrical cautery device is connected by placing a thermal delivery element 20 into the end of the applicator tool tube 18 and securing the thermocouple wire in wiring bundle 22 and securing the wiring bundle 22 with one or more wire guides 100 and connecting the wiring bundle 22 to the thermal delivery element 20. In some embodiments, the applicator tool 50 can be connected to the grounded cable 14 carrying the wiring bundle 22 (not shown) and is connected through a cautery tool connector 32. The foot switch 36 is connected to the controller/power supply 10 through cable 34. The controller/power supply 10 can be connected to a source of electrical current and power (not shown) for operation, preferably including a connection to a GFCI panel to provided protection against leakage ground current in excess of 6 milliamperes.

To heat the tissue in need of heating or cauterization, the surgeon inputs a desired temperature by inputting a numerical value on the temperature input means 12 using the temperature selection buttons 30 and confirming the selection by verifying the preset temperature displayed on the visual temperature indicator 28. The temperature input means 12 can include for example a DIN Microprocessor-Based tuning control. In some embodiments, the temperature input means can be a microprocessor based temperature controller. In some embodiments, the temperature input means also has an alarm to indicate that the temperature preset by the operator has been reaches and/or the temperature at the thermal delivery element has passed the preset temperature. Suitable examples are manufactured by numerous sources and can include, for example, Series 93 1/16 DIN Microprocessor-Based Auto-tuning controller from Watlow Controls, Winona, Minn., USA. The surgeon can also select the percentage of the maximum deliverable power (VAC) by adjusting the voltage selection dial 26. The surgeon can then connect the applicator tool 50 to the controller/power supply 10 via the cautery tool connector 32. Once the controller/power supply is operable to deliver power, the surgeon can actuate the delivery of power to the applicator tool 50 by depressing foot switch 36. In some embodiments, the foot switch 36 can function as a simple on/off switch to apply power, current or voltage from the controller/power supply 10 to the applicator tool 50 and ultimately the thermal delivery element 20 to produce resistive heat in the thermal delivery element 20 via the resistive coil (not shown). In some embodiments, the controller/power supply 10 can be set up to alert the operator or surgeon once a predetermined power, current, voltage is delivered or temperature of the thermal delivery element 20 is reached.

The surgeon or operator can heat tissue, or induce hemostasis and cauterize the tissue by placing a surgical cauterizing device in accordance with the present disclosure that can include a controller/power supply 10, an applicator tool 50 and a flexible thermal delivery element 20 having a planar resistive coil. The surgeon or operator can actuate the cautery device by applying electric power to the thermal delivery element 20 for a period of time sufficient to heat the thermal delivery element 20 to a predetermined temperature. Once the thermal delivery element has reached the predetermined temperature, the thermal delivery element 20 can be pressed against the bleeding tissue for a thermal application interval ranging from 1 second to about 300 seconds to heat and/or cauterize the bleeding tissue being compressed.

In some embodiments, the surgeon or operator can wait for the thermal delivery element 20 to reach a predetermined temperature set by the temperature input means 12 before applying the electrical cautery device against the tissue. In some embodiments, the surgeon or operator can press the thermal delivery element's tissue contact surface against the tissue to be heated while the thermal delivery element 20 reaches the desired temperature, and then for an additional thermal application interval to cauterize the tissue. In some embodiments, the surgeon or operator can actuate the electrical cautery device by pressing on the foot switch 36 which allows the flow of power, current or voltage to the thermal delivery element 20 from the controller/power supply 10.

In some embodiments, the electrical cautery device of the present disclosure can be used to cauterize and provide hemostasis to parenchyma, including for example, liver, lung, spleen and kidney tissue. In some embodiments, the electrical cautery device of the present disclosure can be used to cauterize and provide hemostasis to venous complexes, for example, dorsal venous complex and pre-sacral venous complexes and the like.

The heat generated by the resistive coil in thermal delivery element can be transferred to the tissue being compressed by the electrical cautery device. In some embodiments, compression of the bleeding tissue with the thermal delivery element 20 heated to a predetermined temperature can permit the transfer of substantially all of the heat radiating from the resistive coil within the thermal delivery element to the tissue to cause heating, and/or tissue and blood coagulation. Once the tissue has been heated to a predetermined temperature for a period of time referred to herein as a thermal application interval, the tissue can be visually assessed to determine whether the tissue is under sufficient hemostasis. In some embodiments, cauterization is achieved when proteins are denatured and coagulation of the tissue occurs. In some embodiments, hemostasis is achieved when the tissue surface has been sufficiently coagulated, including the blood vessels, so that hemorrhaging is reduced and/or discontinued.

In some embodiments hemostasis can be experimentally measured. For example, the strength of a coagulation produced on the side of a lacerated blood vessel can be measured experimentally by first producing the coagulation and then applying measured amounts of hydrostatic pressure to the inside of the vessel until the coagulation blows off and bleeding recommences. Collateral thermal damage is also a measurable quantity in that the amount of collateral thermal damage can be readily assessed visually or microscopically. By use of this methodology, a table of optimized parameters could be constructed for any type of tissue. These parameters can be incorporated into the various cauterization protocols including temperature/time combinations by selecting the appropriate factors considered relevant including: power or current to be applied, electrical resistance of the thermal delivery element resistive coil, the maximum wattage density of the thermal heating element (W/in$^2$), the amount of pressure used to press against the hemorrhaging tissue during the coagulating/sealing/joining process, as well as the thermal application interval period of cauterization. Some of the parameters including power output, thermal application interval can simply be inputted into the instrument (i.e., simple mechanical timer, fixed preset voltage and current, and spring-loaded pressure instruments, or, the device can incorporate more flexible and active controls based on microprocessor regulation of the heating process, guided by a "look-up" table in ROM and by using sophisticated mechanical force/pressure sensors and strain gauges). Also, for certain applications, it may be sufficient to have a skilled surgeon or operator, visually or by other sensing means, determine the thermal application period and the amount of pressure required to cause tissue heating and/or cauterization.

In some embodiments, hemostasis may not be achieved in one thermal application. If the tissue continues to hemorrhage, heating and/or cauterization can be repeated on the bleeding tissue by compressing the thermal delivery element 20 against the hemorrhaging tissue and heating the tissue using the electrical cautery device as disclosed herein to a predetermined temperature for another thermal application interval. These steps can be repeated as necessary to achieve satisfactory hemostasis as determined by the surgeon or operator.

In some embodiments, the predetermined temperature can be any temperature that can be useful for cauterizing organic hemorrhaging tissue. In some embodiments the predetermined temperature can be any temperature between 65° C. and 300° C. preferably between 60° C. to 250° C., 80-150° C., 90-130° C. or 100-120° C. The thermal delivery element 20 can be set at a predetermined temperature for example 120° C. and pressed against bleeding tissue for a thermal application interval of 1 to 200 seconds to effect tissue heating and/or cauterization. In some embodiments, the thermal delivery element 20 can be pressed against a tissue set at a predetermined temperature ranging from 100° C. to 150° C. for an thermal application interval ranging from about 10 second to about 120 seconds. The thermal application interval can be adjusted according to many different variables, including, for example, to the amount of power, current or voltage set to be delivered to the thermal delivery element per second, i.e. the composition of the resistive coil of thermal resistance provided by the resistive foil, the wattage density of the resistive coil, the predetermined temperature to be applied against the hemorrhaging tissue, the type of tissue to be cauterized or heated, and combinations thereof.

In some embodiments, the organic tissue to be heated and/ or cauterized, can be any living tissue, for example any mammalian tissue that contains at least one blood vessel, including without limitation, any discreet blood vessel, microvessels, capillaries, veins, arteries and diminutive structures thereof. In some embodiments, the electrical cautery device can be applied against parenchyma tissue comprising arteries and/or veins of varying size within a firm substrate, for example, the functional tissue of an organ such as the kidney, liver, lungs, spleen, and ovaries of an incised tissue and/or organ some embodiments, the electrical cautery device can be applied to structures that include nervous complexes for example the dorsal nervous complexes implicated in prostatectomies and pre-sacral complex implicated in deep pelvic surgeries.

Figure 8:
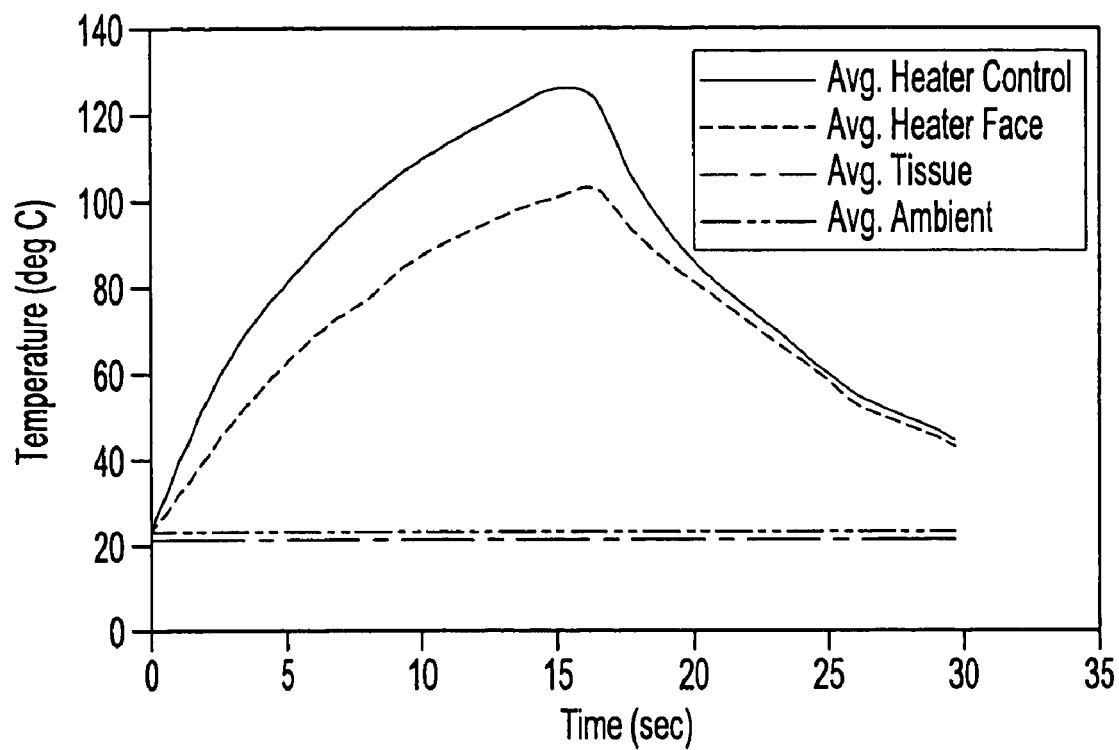
FIG. 8 illustrates an embodiment of the average temperature output of the thermal delivery element (of 5 trials) of the electrical cautery device when used to cauterize porcine liver tissue at room temperature in accordance with the present disclosure.

FIG. 8 illustrates the average performance (of 5 trials) of the electrical cautery device when used to cauterize liver tissue. As can be seen from FIG. 8, the thermal delivery element can provide a heating temperature to the surface of the tissue from 23° C. to about 105° C. in about 16 seconds. In some embodiments, the time spent heating or cauterizing the tissue is referred to as the thermal application interval. The thermal application interval can range from about 1 second to about 240 seconds, from about 15 seconds to about 180 seconds, from about 30 seconds to about 120 seconds, from about 60 seconds to about 100 seconds. In some embodiments, the temperature on the outer tissue surface of the thermal delivery element can be heated to about 250° C., to about 220° C., to about 200° C., to about 180° C., to about 160° C., to about 140° C., to about 120° C., to about 80° C., to about 60° C. and to about 40° C. using the electrical cautery device of the present disclosure.

In order to demonstrate the features and performance of the surgical electrical cautery device and method of surgical cauterization according to the present disclose, a prototype unit, essentially as illustrated in the drawings, FIG. 1-3 was assembled and tested. The following list of equipment was used to assemble the prototype device.

| Device Item | Commercial Source or Description |
| --- | --- |
| Controller/Power Supply | Watlow Series 93 1/16 DIN Microprocessor |
| Resistive coil | Inconel Sacrificial Foil Minco Products Inc. MN USA |
| Thermocouple | Heraeus Model 32208550, M Series Platinum RTD |
| Thermal delivery element | Minco HK 26 461 Kapton heater coated with Kapton/Polyimide and a second outer layer of Fluoro-Ethylene Propylene |
| Foot switch | Mc Master-Carr SPDT moment of contact 7717K24 - Steel Front Hinge |
| GFCI Panel mount | Model 33120 Technology Research Corporation FL, USA |

EXAMPLES

Example 1

Cauterization of Porcine Liver

A flexible thermal delivery element is connected to an applicator tool for thermal heating and cauterization of an incised porcine liver (1×2 cm area) 5 mm deep. The thermal delivery element (Minco #11001A) having a resistance of 199.3Ω was heated using 88.4 VAC for 30 seconds. The thermal curve of the thermal delivery element (average of 5 trials) in contact with the porcine liver is graphically represented in FIG. 8. The predetermined temperature was manually set for 120° C. The maximum tissue contact surface temperature of the thermal delivery element ranged from 98-108° C. when applied on the surface of 23° C. liver tissue for a thermal application period of about 15 seconds. Cauterization penetration depth in porcine liver, ranged from 1.25-2.25 mm.

Example 2

Electro-Cauterization of in-Vivo Porcine Kidney

⅓ resected porcine kidney was electro-cauterized in-vivo with a flexible heater having a kapton/FEP surface coated layers. The experimental animal was anesthetized during the surgical procedure. The thermal delivery element was compressed against the bleeding kidney tissue and heated to about 105-110° C. for 10 seconds per thermal application interval. Substantial hemostasis was achieved after three thermal application intervals of electro-cauterization using the device of the present disclosure. The gross cauterized margin was about 2.0 mm. Essentially, no tissue adhesion to the tissue contact was observed after three applications at 105-110° C.

Example 3

Ablation of Surface Tissue Defect

A surgical process for treating irregular tissue associated with various defective tissue conditions and disorders including tumors, carcinoma in-situ (CIS), adenomas, endometriosis, cervical dysplasias. A laparoscopic device comprising an electrical cautery device as shown in FIGS. 1 and 5A-5C, is introduced into the surgical site of the patient. The tumor bed or tissue defect is localized on the surface of connective or stromal tissue. The tumor or defect is the cauterized (ablated) with one or more applications of heat on the surface of the tumor or tissue defect, to render the tumor or tissue defect destroyed. Operational parameters of the electrical cautery device can be adjusted by altering the predetermined temperature, the duration of the thermal application period and number of applications performed on the tumor or defect to provide ablation of the tumor or defective tissue and to provide hemostasis.

Example 4

Clearance of Microtumors from Tumor Bed after Resection

Residual tumor cells are electrically cauterized after primary tumor removal. The primary tumor is removed surgically by removing substantially all of the primary tumor mass. The margins are biopsied and the surrounding tumor bed after tumor resection is electrically cauterized to provide hemostasis of hemorrhaging tissue and blood vessels. The tumor bed is also cleared of any tumor cells residing after the primary tumor has been removed. The electrical cautery device is used as provided in Examples 1-3 to provide a 1.5-4.0 mm cauterized margin in the surgical bed to ensure destruction of residual tumor cells.

What is claimed is:

1. An apparatus for delivering thermal energy to tissue, the apparatus comprising:
   an electrically powered thermal delivery element configured to be flexible and having a substantially planar resistive coil embedded in a thermally conductive material, wherein the electrically powered thermal delivery element has a tissue contact surface and an opposed non-tissue contact surface, said tissue contact surface operable to directly heat a surface of tissue being contacted by thermal transfer from said substantially planar resistive coil embedded in said thermally conductive material, said thermal delivery element having a maximum watt density of about 5 to about 70 Watts per square inch sufficient to heat said tissue contact surface to a set predetermined temperature, and
   a power generating means connected to said resistive coil of said thermal delivery element generating an electrical current through said thermal delivery element during a thermal application interval having sufficient energy to heat the tissue contact surface of said thermal delivery element to said set predetermined temperature to cauterize said tissue during said application interval;
   wherein the electrically powered thermal delivery element is configured to be flexible by including at least one slit to allow a first portion of the electrically powered thermal delivery element to fold relative to a second portion of the electrically powered thermal delivery element.

2. The apparatus of claim 1, wherein the planar resistive coil has an effective resistance ranging from 50 to 500 ohms/in$^2$ sufficient to heat said thermal delivery element to heat said tissue to the predetermined temperature within the thermal application period.

3. The apparatus of claim 1, further comprising a controller means operably connected to said power generating means to control the output of electrical power from said power generating means to said thermal delivery element comprising a voltage regulator and a temperature controller.

4. The apparatus of claim 1, further comprising a temperature measuring means connected to said non-tissue contact surface of said thermal delivery element and to said controller means for providing an electrical indication of the temperature of said thermal delivery element.

5. The apparatus of claim 1, further comprising an applicator instrument comprising: a generally cylindrical shell having a first end and a second end, said shell comprises a cavity containing an electrical conductor operable to transmit electrical power from said power generating means to said thermal delivery element, a temperature measuring means connected to said thermal delivery element and a controller means,
   a flexible cable operably connected to said first end of said applicator instrument comprising said electrical conductor in connection with said power generating means and extends through said cavity of the cable and cylindrical shell and is connected to said thermal delivery element, and
   a connecting means for connecting said thermal delivery element to the second end of said applicator instrument.

6. The apparatus of claim 5, wherein the temperature measuring means is a thermocouple.

7. The apparatus of claim 5, wherein the applicator instrument is electrically grounded.

8. The apparatus of claim 5, further comprising collapsible arms attached to said thermal delivery element and said applicator instrument, said arms operable to collapse when said thermal delivery element is pressed against a tissue.

9. The apparatus of claim 1, wherein the thermally conductive material comprises a low-tissue-adhesion and bio-inert polymeric material.

10. The apparatus of claim 9, wherein the bio-inert polymeric material comprises any one or more of polytetrafluoroethylene, a derivative of polytetrafluoroethylene, a variant of polytetrafluoroethylene, polyimide, polyvinyl fluoride, polyvinylidene fluoride, perfluoroalkoxy tetrafluoroethylene, polychloro trifluoroethylene and silicone elastomer.

11. A surgical cauterizing device comprising:
   a power generating means providing a source of current or voltage;
   an applicator instrument having a first end and a second end, wherein said first end is in electrical communication with said power source;
   an electrical lead disposed within said applicator instrument;
   a deformable bio-inert heating element operably connected with said second end of said applicator instrument, said heating element having an electrically resistive planar foil encapsulated within a thermally conductive encapsulation material to generate heat to cauterize tissue;
   a thermocouple connected to the deformable bio-inert heating element configured to send a signal based on a temperature of the deformable bio-inert heating element to assist in controlling the power generating means; and
   an instrument defining a lumen;
   wherein said applicator instrument is operable to be moved within said lumen;
   wherein said deformable bio-inert heating element includes a plurality of leaves configured to be folded relative to one another within said lumen.

12. The surgical cauterizing device according to claim 11, further comprising a controller means operably connected to said power source for regulating electrical current.

13. The surgical cauterizing device according to claim 11, wherein the thermocouple is operably connected to said heating element and in electrical communication with said controller means.

14. The surgical cauterizing device according to claim 11, wherein the encapsulation material comprises polyimide.

15. The surgical cauterizing device according to claim 11, wherein the encapsulation material comprises any one or more of polyfluorotetra-ethylene, fluoro-ethylene propylene, polyvinyl fluoride, polyvinylidene fluoride, perfluoroalkoxy tetrafluoroethylene, polychloro trifluoroethylene, and silicone elastomer.

16. The surgical cauterizing device according to claim 15, wherein the encapsulation material includes fluoro-ethylene-propylene and polyimide.

17. The surgical cauterizing device according to claim 11, wherein said planar foil comprises a resistive material having an effective resistance ranging from 50 to 500 ohms/in$^2$.

18. The surgical cauterizing device according to claim 11, wherein said planar foil has a maximum watt density of about 5 to about 70 Watts per square inch sufficient to heat said tissue contact surface to a set predetermined temperature.

* * * * *

UNITED STATES PATENT AND TRADEMARK OFFICE
CERTIFICATE OF CORRECTION

| | |
|---|---|
| PATENT NO. | : 8,202,269 B2 |
| APPLICATION NO. | : 11/807312 |
| DATED | : June 19, 2012 |
| INVENTOR(S) | : J. Stuart Wolf, Jr. et al. |

It is certified that error appears in the above-identified patent and that said Letters Patent is hereby corrected as shown below:

| | |
|---|---|
| Column 1, line 21 | "Million" should be --million--. |
| Column 1, line 43 | After "vessels" insert --to--. |
| Column 3, line 25 | After "steps" insert --:--. |
| Column 3, line 47 | After "view" insert --of--. |
| Column 5, line 56 | After "80" insert --and--. |
| Column 5, line 66 | After "element 20" insert --,--. |
| Column 6, line 66 | After "assembly 70" insert --.--. |
| Column 7, line 25 | "element 20," should be --element 20.--. |
| Column 8, line 5 | "a inner" should be --an inner--. |
| Column 8, line 46 | "FIG. 5A-5C illustrates" should be --FIGS. 5A-5C illustrate--. |
| Column 8, lines 62-63 | "1 inches" should be --1 inch--. |
| Column 9, line 39 | "illustrates" should be --illustrate--. |
| Column 11, line 17 | "to provided" should be --to provide--. |
| Column 11, line 30 | "has been reaches" should be --has been reached--. |
| Column 13, lines 24-25 | "an thermal" should be --a thermal--. |

Signed and Sealed this
Sixth Day of November, 2012

David J. Kappos
*Director of the United States Patent and Trademark Office*

CERTIFICATE OF CORRECTION (continued)
U.S. Pat. No. 8,202,269 B2

| | |
|---|---|
| Column 13, line 25 | "10 second" should be --10 seconds--. |
| Column 13, line 31 | "resistive foil" should be --resistive coil--. |
| Column 13, line 44 | After "and/or" delete "organ". |
| Column 14, line 1 | "present disclose" should be --present disclosure--. |
| Column 14, line 49 | "kapton/FEP" should be --Kapton/FEP--. |
| Column 16, line 52, Claim 11 | "foil" should be --coil--. |
| Column 18, line 5, Claim 17 | "foil" should be --coil--. |
| Column 18, line 8, Claim 18 | "foil" should be --coil--. |